United States Patent [19]

Breuer et al.

[11] 3,991,051

[45] Nov. 9, 1976

[54] [(OXYALKYL)THIOACETYL]CEPHALOSPORIN DERIVATIVES

[75] Inventors: Hermann Breuer; Uwe D. Treuner, both of Regensburg, Germany

[73] Assignee: E. R. Squibb & Sons, Inc., Princeton, N.J.

[22] Filed: May 1, 1975

[21] Appl. No.: 573,676

[52] U.S. Cl. ............................ 260/243 C; 260/470; 260/481 R; 260/516; 260/535 S; 260/544 Y; 424/246
[51] Int. Cl.$^2$ ................ C07D 501/28; C07D 501/32
[58] Field of Search ................................ 260/243 C

[56] References Cited
UNITED STATES PATENTS 3,338,897  8/1967  Takano et al. .................. 260/243 C

FOREIGN PATENTS OR APPLICATIONS 2,304,226  8/1973  Germany ......................... 260/243 C

OTHER PUBLICATIONS

Sassiver et al., Antimicrobial Agents & Chemeotherapy, 1968, pp. 101–108 (1969).

Primary Examiner—Nicholas S. Rizzo
Assistant Examiner—Diana G. Rivers
Attorney, Agent, or Firm—Lawrence S. Levinson; Merle J. Smith

[57] ABSTRACT

[(Oxyalkyl)thioacetyl]cephalosporin derivatives having the formula

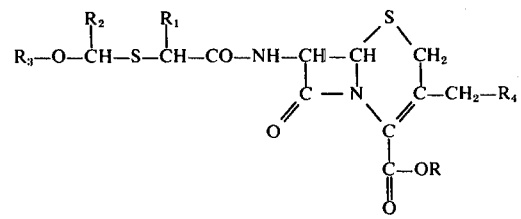

wherein R is hydrogen, lower alkyl, phenyl-lower alkyl, tri(lower alkyl)silyl, a salt forming ion, or the group

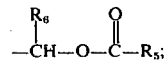

$R_1$ is hydrogen, lower alkyl, phenyl, thienyl or furyl; $R_2$ and $R_6$ each is hydrogen or lower alkyl; $R_3$ and $R_5$ each is lower alkyl, phenyl or phenyl-lower alkyl; and $R_4$ is hydrogen, hydroxy, lower alkanoyloxy, lower alkoxy or lower alkylthio; are useful as antimicrobial agents.

10 Claims, No Drawings

[(OXYALKYL)THIOACETYL]CEPHALOSPORIN DERIVATIVES

SUMMARY OF THE INVENTION

This invention relates to new [(oxyalkyl)thioacetyl]-cephalosporin derivatives having the formula

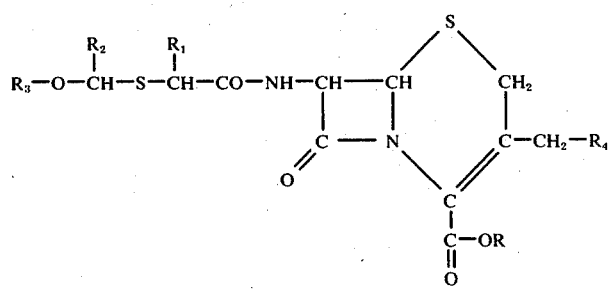

R represents hydrogen, lower alkyl, phenyl-lower alkyl, tri(lower alkyl)silyl, a salt forming ion or the group

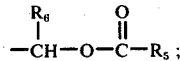

$R_1$ represents hydrogen, lower alkyl, phenyl, thienyl or furyl; $R_2$ and $R_6$ each represents hydrogen or lower alkyl; $R_3$ and $R_5$ each represents lower alkyl, phenyl or phenyl-lower alkyl; and $R_4$ represents hydrogen, hydroxy, lower alkanoyloxy, lower alkoxy or lower alkylthio.

The especially preferred members within each group are as follows: R is hydrogen, alkali metal, diphenylmethyl or

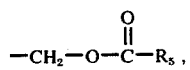

especially hydrogen, pivaloyloxy, sodium or potassium; $R_1$ is hydrogen or phenyl; $R_2$ is hydrogen; $R_3$ is lower alkyl, especially methyl; $R_4$ is hydrogen or acetoxy; and $R_5$ is methyl or t-butyl.

DETAILED DESCRIPTION OF THE INVENTION

The various groups represented by the symbols have the meanings defined below and these definitions are retained throughout this specification.

The lower alkyl groups are the straight and branched chain hydrocarbon groups in the series from methyl to heptyl, the $C_1$ to $C_4$ groups and especially methyl and ethyl being generally preferred. The lower alkoxy and lower alkylthio groups are of the same type and the same preferences apply.

The lower alkanoyloxy groups represented by $R_4$ include the acyl radicals of lower fatty acids containing alkyl radicals of the type described above, e.g., acetoxy, propionoxy, butyryloxy, etc., the $C_1$ to $C_4$ members being preferred and acetoxy being especially preferred.

The phenyl-lower alkyl radicals include a phenyl ring attached to a lower alkyl group of the kind described above like benzyl and phenethyl as well as those containing two phenyl groups such as diphenylmethyl.

The salt forming ions represented by R are metal ions, e.g., alkali metal ions such as sodium or potassium, alkaline earth metal ions such as calcium or magnesium or an amine salt ion, e.g., a (lower alkyl)amine like methylamine or triethylamine.

The new [(oxyalkyl)thioacetyl]cephalosporin derivatives of this invention are produced by reacting a 7-aminocephalosporanic acid compound, e.g., 7-aminocephalosporanic acid (7-ACA), 7-amino-3-desacetoxycephalosporanic acid (7-ADCA) and other derivatives, having the formula

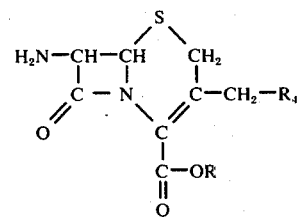

or derivatives thereof with an [(oxyalkyl)thio]acetic acid of the formula

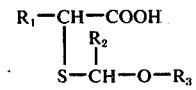

or an acid halide, anhydride including mixed anhydrides, activated esters or the like.

The derivatives of II referred to include, for example, the triethylamine derivative, benzhydryl ester or the like. The acid halide of III is preferably the chloride. Coupling agents like dicyclohexylcarbodiimide or the like can also be used.

A preferred method is the reaction between the 7-aminocephalosporanic acid compound and the [(oxyalkyl)-thio]acetic acid, for example, by dissolving or suspending the latter in an inert organic solvent such as chloroform, tetrahydrofuran, methylene chloride, dioxane, benzene or the like, and adding, at a reduced temperature of about 0° to −20° C about an equimolar amount of the 7-ACA or 7-ADCA compound, preferably in the form of its diphenylmethyl ester, in the presence of an activating compound such as dicyclohexylcarbodiimide. The product of the reaction is then isolated by conventional procedures, e.g., by filtration and concentration or evaporation of the solvent. The diphenylmethyl ester is converted to the free acid, e.g., with trifluoroacetic acid and anisole. Any of the salts can then be produced by conventional treatment, e.g., with potassium ethyl hexanoate, sodium bicarbonate or the like.

Another preferred method involves the reaction of a 7-aminocephalosporanic acid compound with the acid halide of the [(oxyalkyl)thio]acetic acid in aqueous alkaline medium.

When R is the acyloxymethyl group

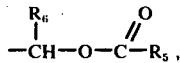

this group may be introduced into the 7-aminocephalosporanic acid moiety prior to the reaction with the [(oxyalkyl)thio]-acetic acid or derivative by treatment with one to two moles of a halomethyl ester of the formula

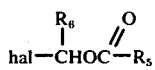 (IV)

wherein hal is halogen, preferably chlorine or bromine, in an inert organic solvent such as dimethylformamide, acetone, dioxane, benzene or the like, at about ambient temperature or below.

The [(oxyalkyl)thio]acetic acid of formula III is produced by reacting a mercaptoacetic acid of the formula

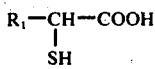 (V)

with a halogenated compound of the formula

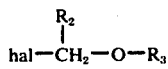 (VI)

in the presence of a base like triethylamine in a solvent like tetrahydrofuran and then hydrolyzing the ester formed in the process.

Alternatively, when the acid halide is used to react with the 7-aminocephalosporanic acid compound, an alkoxide $R_3$-OMe (wherein Me is a metal like sodium or potassium) is made to react with a haloester of the formula

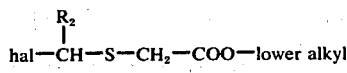 (VII)

to obtain the intermediate of the formula

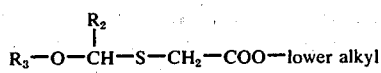 (VIII)

Treatment with a base, e.g., an alkali metal hydroxide like potassium hydroxide, converts the ester to a salt which is then converted to the acid chloride with a halogenating agent like oxalyl chloride.

Further process details are provided in the illustrative examples.

Certain of the compounds of this invention may exist in different optically active forms. The various stereoisomeric forms as well as the racemic mixtures are within the scope of the invention.

The compounds of this invention have a broad spectrum of antibacterial activity against both gram positive and gram negative organisms such as *Staphylococcus aureus*, *Salmonella schottmuelleri*, *Pseudomonas aeruginosa*, *Proteus vulgaris*, *Escherichia coli* and *Streptococcus pyrogenes*. They can be used as antibacterial agents to combat infections due to organisms such as those named above, and in general may be utilized in a manner similar to cephradine and other cephalosporins. For example, a compound of formula I or a physiologically acceptable salt thereof can be used in various animal species in an amount of about 1 to 150 mg/kg, daily, orally or parenterally, in single or two to four divided doses to treat infections of bacterial origin, e.g., 7.0 mg/kg is used in mice.

Up to about 600 mg. of a compound of formula I or a physiologically acceptable salt thereof is incorporated in an oral dosage form such as tablets, capsules or elixirs or in an injectable form in a sterile aqueous vehicle prepared according to conventional pharmaceutical practice.

The following examples are illustrative of the invention. All temperatures are in degrees celsius. Additional variations are produced in the same manner by appropriate substitution in the starting material.

EXAMPLE 1

154.6 g. (1 mol.) of [(chloromethyl)thio]acetic acid methyl ester are dissolved in 1000 ml. of absolute methanol, cooled to −30° and, at this temperature, 500 ml. of a 2N sodium methoxide solution is added dropwise. The reaction mixture is stirred for three more hours at 0° and 10 g. of glacial acetic acid are added. The precipitate is filtered off under suction and the filtrate is concentrated. 1 liter of ether is added to the residue and additional precipitate is filtered off. The solvent is evaporated off and the residue is fractionated under vacuum. After distilling twice, the yield of [(methoxymethyl)thio]acetic acid methyl ester is 30.3 g., b.p. 85°–90° (10 mm).

EXAMPLE 2

2.4 g. (0.016 mol.) [(methoxymethyl)thio]acetic acid methyl ester are dissolved in 20 ml. of isopropanol and 10 ml. of a 2N solution of potassium hydroxide in methanol are added. The reaction mixture is let stand for two hours at room temperature and one hour in the refrigerator, then the crystalline [(methoxymethyl)thio]acetic acid potassium salt which has formed is filtered under suction, yield 2.0 g., m.p. > 250°.

EXAMPLE 3

8.7 g. (0.05 mol.) of [(methoxymethyl)thio]acetic acid potassium salt are finely divided and suspended in 50 ml. of methylene chloride. 0.1 ml. of pyridine is added and then a solution of 12.6 g. (0.1 mol.) of oxalyl chloride in 16 ml. of methylene chloride are added dropwise at room temperature with stirring. The mixture is stirred for an additional three hours. This is then concentrated, absolute ether is added to the residue, the filtrate is again concentrated and the oily residue, [(methoxymethyl)thio]acetyl chloride, is distilled in vacuo, yield 3.6 g., b.p. 40°–42° (0.05 mm).

EXAMPLE 4

2.7 g. (0.01 mol.) of 7-aminocephalosporanic acid (7-ACA) are suspended in a mixture of 30 ml. of water and 30 ml. of acetone and brought into solution by the addition of 1.5 ml. of triethylamine. The solution is cooled to 0°–5° and a solution of 2.0 g. of [(methoxymethyl)-thio]acetyl chloride in 10 ml. of anhydrous acetone is added dropwise with stirring. By the simultaneous addition of triethylamine dissolved in a little acetone, the pH of the solution is kept at 7.5. The reaction mixture is stirred for 30 minutes more. Then ethyl acetate and water are added and acidified to pH 2 with 2N hydrochloric acid. The ethyl acetate phase is washed several times with water, dried with magnesium sulfate and concentrated. 4 g. of 3-[(acetyloxy)-methyl]-7β-[[[(methoxymethyl)thio]acetyl]amino]-8-oxo-5-thia-1-azabicyclo[4.2.0]oct-2-ene-2-carboxylic acid are obtained as a yellow-brown syrup.

EXAMPLE 5

The crude product from Example 4 is dissolved in 15 ml. of methanol and 5 ml. of a 2N solution of potassium ethylhexanoate are added. 3-[(acetyloxy)methyl]-7β-[[[(methoxymethyl)thio]acetyl]amino]-8-oxo-5-thia-1-azabicyclo[4.2.0]-oct-2-ene-2-carboxylic acid, potassium salt crystallizes and is filtered under suction, yield 2.1 g., m.p. 117°–119° (dec.).

EXAMPLE 6

16.8 g. (0.1 mol.) of α-mercaptobenzeneacetic acid are dissolved in 100 ml. of anhydrous tetrahydrofuran and 24 g. (0.3 mol.) of chloroacetone are added. This is cooled to 0° and 41.4 ml. of triethylamine are added dropwise under nitrogen. The mixture is stirred overnight at room temperature, then washed with water, sodium bicarbonate solution and more water. The solution is dried with magnesium sulfate, the solvent is evaporated and the residue is distilled in vacuo. The yield of α-[(methoxymethyl)thio]benzeneacetic acid methoxymethyl ester is 16.7 g., b.p. 132°–135° (0.1 mm).

EXAMPLE 7

2.56 g. (0.01 mol.) of α-[(methoxymethyl)thio]-benzeneacetic acid methoxymethyl ester are dissolved in 10 ml. of methanol and 10 ml. of 2N methanolic potassium hydroxide solution are added. The reaction mixture is let stand overnight. The solvent is evaporated and water is added to the solid residue. This is extracted once with ether. The aqueous phase is acidified and the oil which separates is taken up with water and dried with magnesium sulfate. After evaporating the solvent, 2.1 g. of α-[(methoxymethyl)thio]benzeneacetic acid remains as an oily residue.

EXAMPLE 8

2.19 g. (0.005 mol.) of 7-aminocephalosporanic acid diphenylmethyl ester and 1.30 g. (0.006 mol.) of α-[(methoxymethyl)thio]benzeneacetic acid are dissolved in 100 ml. of tetrahydrofuran, cooled to 0°–5° and a solution of 1.13 g. (0.0055 mol.) of dicyclohexylcarbodiimide in 10 ml. of tetrahydrofuran are added dropwise with stirring. The mixture is stirred for 90 minutes at 0°–5° and 90 minutes at room temperature. The mixture is then filtered and the filtrate is concentrated. The residue is taken up with ethyl acetate, washed with sodium bicarbonate solution and with water, dried with magnesium sulfate and concentrated. The oily residue 3-[(acetyloxy)methyl]-7β-[[[(methoxymethyl)-thio]phenylacetyl]amino]-8-oxo-5-thia-1-azabicyclo[4.2.0]oct-2-ene-2-carboxylic acid diphenylmethyl ester, crystallizes upon trituration with petroleum ether, yield 1.8 g., m.p. 93°–102°.

EXAMPLE 9

1.6 g. of the product of Example 8 are added at 0°–5° to a mixture of 36 ml. of trifluoroacetic acid and 11 ml. of anisole. The mixture is stirred for 10 minutes and concentrated in vacuo. The residue is taken up with a little ethyl acetate, the acid is extracted with sodium bicarbonate solution and the aqueous phase is acidified. The precipitated 3-[(acetyloxy)methyl]-7β-[[[(methoxymethyl)thio]phenylacetyl]-amino]-8-oxo-5-thia-1-azabicyclo[4.2.0]oct-2-ene-2-carboxylic acid is taken up with ethyl acetate, washed with water, dried with magnesium sulfate and concentrated. The oily, residual product crystallizes upon trituration with petroleum ether, yield 0.9 g., m.p. < 55° (dec.).

EXAMPLE 10

0.9 g. (0.0019 mol.) of the product of Example 9 are dissolved in 20 ml. of methanol and 19 ml. of 0.1N sodium bicarbonate solution are added. The methanol is evaporated, the aqueous solution is filtered and freeze dried to obtain 0.7 g. of 3-[(acetyloxy)methyl]-7β-[[[(methoxymethyl)thio]phenylacetyl]amino]-8-oxo-5-thia-1-azabicyclo[4.2.0]oct-2-ene-2-carboxylic acid sodium salt, decomposes below 125°.

The following additional products having the formula (c) in the table are obtained by the procedure of Examples 8, 9 and 10 by substituting for the 7-aminocephalosporanic acid, diphenylmethyl ester, the starting material (a), and for the α-[(methoxymethyl)thio]benzeneacetic acid, the starting material (b) with the substituents indicated in the table:

TABLE

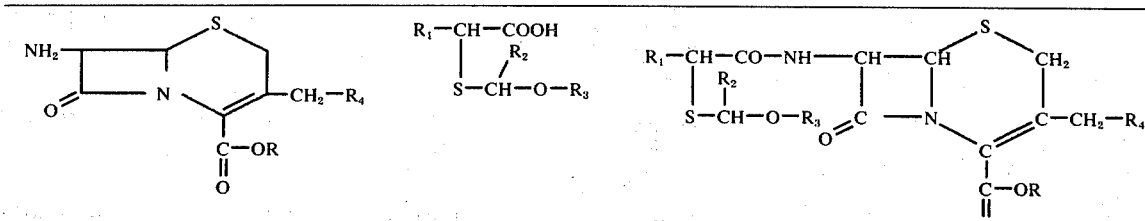

| Example | R | $R_1$ | $R_2$ | $R_3$ | $R_4$ |
|---|---|---|---|---|---|
| 19 | —CH$_3$ | H | —C$_3$H$_7$ | —C$_3$H$_7$ | H |
| 20 | —C$_2$H$_5$ | —CH$_3$ | —C$_2$H$_5$ | —CH$_3$ | —OH |
| 21 | —CH$_2$C$_6$H$_5$ | —C$_3$H$_7$ | H | —C$_2$H$_5$ | —OCOCH$_3$ |

TABLE-continued

Structure (a): 7-amino cephalosporin with NH$_2$, S ring, $-CH_2-R_4$, $-COOR$

Structure (b): $R_1-CH(COOH)-S-CH(R_2)-O-R_3$

Structure (c): $R_1-CH(-CO-NH-CH-...)-S-CH(R_2)-O-R_3$, coupled to cephem with $-CH_2-R_4$ and $-COOR$

| Example | (a) R | (b) R$_1$ | R$_2$ | R$_3$ | (c) R$_4$ |
|---|---|---|---|---|---|
| 22 | $-CH_2OC(O)-CH(CH_3)_2$ | $-C_6H_5$ | H | $-CH_2C_6H_5$ | $-OCOCH_3$ |
| 23 | $-CH_2OC(O)-C_6H_5$ | $-C_6H_5$ | $-CH_3$ | $-CH_3$ | $-OCOCH_3$ |
| 24 | $-C_2H_4$-C$_6$H$_5$ | $-C_6H_5$ | $-C_2H_5$ | $-CH_3$ | H |
| 25 | $-CH(C_6H_5)_2$ | thienyl | $-C_2H_5$ | $-CH_3$ | $-OCOCH_3$ |
| 26 | $-Si(CH_3)_3$ | furyl | H | $-C_2H_5$ | H |
| 27 | $-CH(CH_3)-O-C(O)-CH_2-C_6H_5$ | thienyl | H | $-C_6H_5$ | H |
| 28 | $Si(CH_3)_3$ | $-C_6H_5$ | H | $-C_2H_5$ | OH |
| 29 | $C_6H_5CH_2-$ | $-C_6H_5$ | H | $-C_6H_5$ | $-OCOCH_3$ |
| 30 | H | thienyl | $-CH_3$ | $-CH_3$ | $-OCOCH_3$ |
| 31 | Na | furyl | H | $-C_6H_5$ | OH |
| 32 | K | thienyl | H | $-CH_3$ | $-OCH_3$ |
| 33 | H | furyl | $-C_2H_5$ | $-C_6H_5$ | $-OCOCH_3$ |
| 34 | H | thienyl | $-C_2H_5$ | $-CH_3$ | $-OCOCH_3$ |
| 35 | $-CH(C_6H_5)_2$ | thienyl | H | $-C_6H_5$ | H |
| 36 | H | $-C_6H_5$ | H | $-CH_3$ | $-OCH_3$ |

TABLE-continued

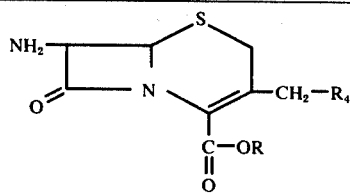  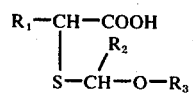  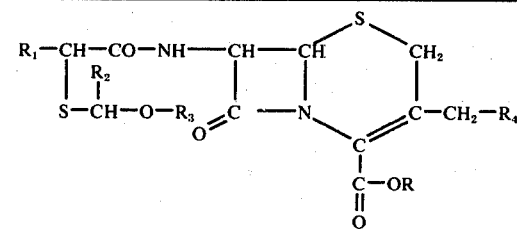

| Example | (a) R | (b) R$_1$ | R$_2$ | R$_3$ | (c) R$_4$ |
|---------|---|-----|-------|-------|-------|
| 37 | K | —C$_6$H$_5$ | H | —CH$_3$ | —SCH$_3$ |
| 38 | H |  (thienyl) | H | —C$_2$H$_5$ | —OCH$_3$ |
| 39 | K |  (thienyl) | —CH$_3$ | —CH$_3$ | —SCH$_3$ |
| 40 | H |  (furyl) | —CH$_3$ | H | —OCH$_3$ |
| 41 | Na |  (furyl) | H | —CH$_3$ | —SC$_2$H$_5$ |
| 42 | H | H | —CH$_3$ | —CH$_3$ | —SCH$_3$ |
| 43 | H | H | H | —CH$_3$ | —OCH$_3$ |
| 44 | H |  (thienyl) | H | —CH$_3$ | —OCOCH$_3$ |
| 45 | H | —C$_6$H$_5$ | H | —CH$_3$ | H |

What is claimed is:

1. A compound of the formula

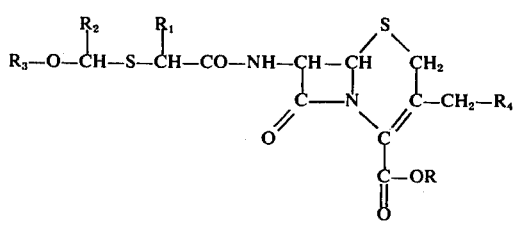

wherein R is hydrogen, lower alkyl, diphenyl-lower alkyl, phenyl-lower alkyl, tri(lower alkyl)silyl,

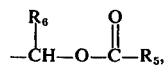

alkali metal, alkaline earth metal, tri(lower alkyl)amine or (lower alkyl)amine; R$_1$ is hydrogen, lower alkyl, phenyl, thienyl or furyl; R$_2$ and R$_6$ each is hydrogen or lower alkyl; R$_3$ and R$_5$ each is lower alkyl, phenyl or phenyl-lower alkyl; and R$_4$ is hydrogen, hydroxy, lower alkanoyloxy, lower alkoxy or lower alkylthio; said lower alkyl, lower alkanoyloxy, lower alkoxy and lower alkylthio groups having up to seven carbons.

2. A compound as in claim 1 wherein R is hydrogen, alkali metal, diphenylmethyl or

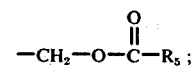

R$_1$ is hydrogen or phenyl; R$_2$ is hydrogen; R$_3$ is lower alkyl; R$_4$ is hydrogen or acetoxy; and R$_5$ is methyl or t-butyl.

3. A compound as in claim 1 wherein R, R$_1$ and R$_2$ each is hydrogen, R$_3$ is lower alkyl and R$_4$ is lower alkanoyloxy.

4. A compound as in claim 1 wherein the lower alkyl group is methyl and the lower alkanoyloxy group is acetoxy.

5. Alkali metal salt of the compound of claim 4.

6. A compound as in claim 1 wherein R and R$_2$ each is hydrogen; R$_1$ is phenyl; R$_3$ is lower alkyl and R$_4$ is lower alkanoyloxy.

7. A compound as in claim 6 wherein the lower alkyl group is methyl and the lower alkanoyloxy group is acetoxy.

8. Alkali metal salt of the compound of claim 7.

9. A compound as in claim 1 wherein R and R$_2$ each is hydrogen; R$_1$ is thienyl; R$_3$ is lower alkyl and R$_4$ is lower alkanoyloxy.

10. A compound as in claim 9 wherein the lower alkyl group is methyl and the lower alkanoyloxy group is acetoxy.

* * * * *